United States Patent
Fa et al.

(10) Patent No.: US 12,270,025 B2
(45) Date of Patent: Apr. 8, 2025

(54) APTAMER OF NATTOKINASE AND METHOD FOR SCREENING THE APTAMER

(71) Applicant: Qingdao Institute of Bioenergy and Bioprocess Technology, Chinese Academy of Sciences, Qingdao (CN)

(72) Inventors: Yun Fa, Qingdao (CN); Haijie Zhao, Qingdao (CN); Mingyang Guan, Qingdao (CN); Qi Wang, Qingdao (CN); Huizhou Liu, Qingdao (CN)

(73) Assignee: Qingdao Institute of Bioenergy and Bioprocess Technology, Chinese Academy of Sciences, Qingdao (CN)

( * ) Notice: Subject to any disclaimer, the term of this patent is extended or adjusted under 35 U.S.C. 154(b) by 1058 days.

(21) Appl. No.: 17/203,781

(22) Filed: Mar. 17, 2021

(65) Prior Publication Data

US 2021/0207128 A1 Jul. 8, 2021

Related U.S. Application Data

(63) Continuation of application No. PCT/CN2020/090634, filed on May 15, 2020.

(30) Foreign Application Priority Data

Apr. 16, 2019 (CN) .......................... 201910305002.4

(51) Int. Cl.
*C12N 15/10* (2006.01)
*C12N 15/115* (2010.01)

(52) U.S. Cl.
CPC ........ *C12N 15/1048* (2013.01); *C12N 15/115* (2013.01); *C12N 2310/16* (2013.01)

(58) Field of Classification Search
None
See application file for complete search history.

(56) References Cited

FOREIGN PATENT DOCUMENTS

| CN | 1188516 C | 2/2005 |
| CN | 103571845 A | 2/2014 |
| CN | 104131105 A | 11/2014 |
| CN | 106636108 A | 5/2017 |

OTHER PUBLICATIONS

Progress in separation and purification of nattokinase and its enzyme activity determination.
Selection and identification of a novel DNA aptamer against CD20 molecule.
Screening and identification of a novel DNA aptamer against albumin.

*Primary Examiner* — Kaijiang Zhang
(74) *Attorney, Agent, or Firm* — Nitin Kaushik

(57) ABSTRACT

An aptamer of nattokinase and method for screening the aptamer are provided, which relate to technical fields of biotechnology. A set of nattokinase nucleic acid aptamers screened by capillary electrophoresis separation technology is: SEQ ID NO:1~SEQ ID NO:17. The dissociation constants of the seven aptamers were detected by surface plasmon resonance technology, and the affinity of the seven aptamers was strong, with affinities between 8.7-87 nM. The nucleic acid aptamer of the present disclosure has precise specificity, high affinity, and is convenient for chemical modification, and can be used as an effective molecular recognition tool for the high-sensitive analysis of proteins. it. The recognition technology based on nucleic acid aptamers provides a basis for the development of NK determination and efficient separation and purification.

2 Claims, 10 Drawing Sheets

Specification includes a Sequence Listing.

SEQUENCE LISTING

<160> NUMBER OF SEQ ID NOS: 24

<210> SEQ ID NO 1
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 1
cgcctgaggg atgacctgtt catgtaggg                29

<210> SEQ ID NO 2
<211> LENGTH: 29
<212> TYPE: DNA
<213> ORGANISM: Artificial Sequence

```
<220> FEATURE:
<223> OTHER INFORMATION: This sequence is synthesized

<400> SEQUENCE: 2
gactaccgcg gagatctcca atcgggatg                                29

<210> SEQ ID NO 3
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 3
aaatgaggac ctcattatct taggaaggt                                29

<210> SEQ ID NO 4
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 4
gccttaaaaa cgtccttagt gacgtttac                                29

<210> SEQ ID NO 5
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 5
gctcacgtag attaaactat gctaagagc                                29

<210> SEQ ID NO 6
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 6
cattgcaatg taactgtcta gcttgactg                                29

<210> SEQ ID NO 7
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 7
ccggtcgcca tgggggagct gcgtaccgc                                29

<210> SEQ ID NO 8
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 8
ccattccaac tcgctttaaa cataaatcg                                29
```

<210> SEQ ID NO 9
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 9
ctgtgaacca aggattcatg ccggtaaac					29

<210> SEQ ID NO 10
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 10
gggttacgat cagtctcatg gaaacgacc					29

<210> SEQ ID NO 11
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 11
gttgcaagga aagctatgcc tatgcccca					29

<210> SEQ ID NO 12
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 12
ctcgtgtaaa acgatggtag ctgtacttg					29

<210> SEQ ID NO 13
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 13
aaaggcgctg tgcacagtgt ccccgcggg					29

<210> SEQ ID NO 14
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 14
ccgaggggaa ttcaccacga atcgcctct					29

<210> SEQ ID NO 15
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 15
tcgatagttg tactggagtg aatcactga                                                29

<210> SEQ ID NO 16
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 16
aagactccag tcgcggcctc tatccggga                                                29

<210> SEQ ID NO 17
<211> LENGTH: 29
<212> TYPE: DNA
<213> ORGANISM: Artificial Sequence
<220> FEATURE:
<223> OTHER INFORMATION: This sequence is synthesized

<400> SEQUENCE: 17
acccaagtag gcgagttcag aactgtgtg                                                29

<210> SEQ ID NO 18
<211> LENGTH: 20
<212> TYPE: DNA
<213> ORGANISM: Artificial Sequence
<220> FEATURE:
<223> OTHER INFORMATION: This sequence is synthesized

<400> SEQUENCE: 18
acgacgagac acctgacatc                                                          20

<210> SEQ ID NO 19
<211> LENGTH: 20
<212> TYPE: DNA
<213> ORGANISM: Artificial Sequence
<220> FEATURE:
<223> OTHER INFORMATION: This sequence is synthesized

<400> SEQUENCE: 19
ttgagcctac gagcgatacc                                                          20

<210> SEQ ID NO 20
<211> LENGTH: 78
<212> TYPE: DNA
<213> ORGANISM: Artificial Sequence
<220> FEATURE:
<223> OTHER INFORMATION: This sequence is synthesized

<400> SEQUENCE: 20
ttgagcctac gagcgatacc gagtgacaat cgacacatat tagtatcttc aacccgtaga             60
tgtcaggtgt ctcgtcgt                                                            78

<210> SEQ ID NO 21
<211> LENGTH: 80
<212> TYPE: DNA
<213> ORGANISM: Artificial Sequence
<220> FEATURE:
<223> OTHER INFORMATION: This sequence is synthesized
<220> FEATURE:
<221> NAME/KEY: misc_feature
<222> LOCATION: (21)..(60)
<223> OTHER INFORMATION: n is a, c, g, or t

<400> SEQUENCE: 21

```
ttgagcctac gagcgatacc nnnnnnnnnn nnnnnnnnnn nnnnnnnnnn nnnnnnnnnn    60
gatgtcaggt gtctcgtcgt                                                 80
```

<210> SEQ ID NO 22
<211> LENGTH: 69
<212> TYPE: DNA
<213> ORGANISM: Artificial Sequence
<220> FEATURE:
<223> OTHER INFORMATION: This sequence is synthesized
<220> FEATURE:
<221> NAME/KEY: misc_feature
<222> LOCATION: (21)..(49)
<223> OTHER INFORMATION: n is a, c, g, or t

<400> SEQUENCE: 22

```
ttgagcctac gagcgatacc nnnnnnnnnn nnnnnnnnnn nnnnnnnnng atgtcaggtg    60
tctcgtcgt                                                             69
```

<210> SEQ ID NO 23
<211> LENGTH: 20
<212> TYPE: DNA
<213> ORGANISM: Artificial Sequence
<220> FEATURE:
<223> OTHER INFORMATION: This sequence is synthesized

<400> SEQUENCE: 23

```
agcagcacag aggtcagatg                                                 20
```

<210> SEQ ID NO 24
<211> LENGTH: 20
<212> TYPE: DNA
<213> ORGANISM: Artificial Sequence
<220> FEATURE:
<223> OTHER INFORMATION: This sequence is synthesized

<400> SEQUENCE: 24

```
ttcacggtag cacgcatagg                                                 20
```

APTAMER OF NATTOKINASE AND METHOD FOR SCREENING THE APTAMER

CROSS-REFERENCE TO RELATED APPLICATIONS

The application claims priority to Chinese patent application No. 201910305002.4, filed on Apr. 16, 2019, the entire contents of which are incorporated herein by reference.

TECHNICAL FIELD

The present disclosure relates to technical fields of biological engineering, inparticular to aptamer of nattokinase and method for screening the aptamer.

BACKGROUND

At present, magnetic microsphere screening method is common in protein screening. Target protein is immobilized on the surface of magnetic beads, and oligonucleotide molecules are diffused freely in liquid. Oligonucleotide molecules are able to bind to the target protein when they meet. In this way, bound or unbound weak oligonucleotide molecules can be separated and removed. The oligonucleotide chain bound to the target is eluted and separated, and then perform the next cycle of PCR amplification. However, the method requires multiple cycles, time-consuming and is prone to causing non-specific adsorption.

Nattokinase (NK) is a thrombolytic agent with high fibrinolytic activity, safety and economy. NK activity is greatly affected by external factors, so the application of the quantitative determination method of nattokinase activity is greatly restricted, especially in the study of efficient separation and purification and thrombolytic mechanism.

The fibrin plate method is the most popular method among scientists for determining NK enzyme activity. In this method, the fibrinolytic activity is calculated quantitatively based on the area of the dissolving ring. The detection result of this method is affected by time, temperature and product purity, resulting in large errors in detection data and low sensitivity. Moreover, due to the high prices of fibrin sources and thrombin, it is difficult to reduce the cost of testing. This fibrin plate method is used by scientists in many countries, such as China, Japan, India, South Korea and Canada. In addition, enzyme-linked immunosorbent assay is used by a small number of Japanese scientists. Although there are many methods for determining NK, there is no uniform standard.

The limitations of various enzyme activity detection methods lead to differences in experimental results, making the experimental results unable to be compared with each other. In the production, separation and purification experiments of nattokinase, the physical and chemical properties (such as molecular weight) of nattokinase prepared by different strains and different fermentation processes are different, which leads to inaccurate determination results and difficult separation operations.

In practical applications, the detection result of enzyme activity does not directly reflect the true yield of NK, which has led to the limitation of the large-scale production and development and application of NK as a thrombolytic agent.

In summary, the problems in the prior art are described as follows.

(1) In prior art, the limitations of various enzyme activity detection methods lead to differences in experimental results, making the experimental results unable to be compared with each other. In the production, separation and purification experiments of nattokinase, the physical and chemical properties (such as molecular weight) of nattokinase prepared by different strains and different fermentation processes are different, which leads to inaccurate determination results and difficult separation operations.

(2) Pure products are difficult to obtain because the properties of nattokinase are not stable enough. Traditional methods are still used for enzyme activity determination.

(3) Traditional screening methods have the disadvantages of cumbersome operation, time-consuming, low efficiency and poor repeatability.

SUMMARY

In view of the above problems in the prior art, the present disclosure provides aptamer of nattokinase and method for screening the aptamer, so as to solve some problems or at least alleviate some problems in the prior art.

The disclosure is realized by the following technical scheme:

a method for screening nattokinase nucleic acid aptamer, comprising the following steps of:

designing and constructing a random oligonucleotide library with fixed sequences at both ends;

mixing the random oligonucleotide library with nattokinase, incubating the mixture, performing capillary electrophoresis separation, and collecting the bound complexes;

using the collected bound complexes as a template for asymmetric PCR amplification and preparing a secondary library;

conducting multiple rounds of screening of secondary libraries, using the complexes obtained in the last round of screening for PCR amplification to obtain a nucleotide library that binds to nattokinase;

sequencing the nucleotide library after purification to obtain candidate aptamers;

testing the structure, affinity and specificity of candidate aptamers to obtain high affinity and high specificity nattokinase nucleic acid aptamers.

Further, a condition of the capillary electrophoresis separation is as following: capillary temperature is 25° C., 0.5 psi, 20 s injection, separation voltage is 25 kV, a running buffer of the capillary electrophoresis is 50 mmol/L boric acid-borax buffer with pH 7.8, a detection wavelength is 280 nm.

Further, in the capillary electrophoresis separation process, nattokinase peaking at 3.3 min, ssDNA peaking at 9.9 min, and the peak of NK-ssDNA complex appearing at 15.2 min, and a collection time is 18.76 min-24.56 min.

Further, combining a 69 nt random sequence library with nattokinase, the 69 nt random sequence is 5'-TTGAGCC-TACGAGCGATACC-29N-GATGTCAGGTGTCTCGTCGT-3', where 29N means that there are 29 random sequences of T, G, A or C.

Further, a pair of primer sequences involved in the asymmetric PCR are shown in SEQ ID NO: 18 and SEQ ID NO: 19, respectively, wherein a concentration of downstream primer is 0.5 µmol/L, and a ratio of upstream and downstream primers is 30:1.

Preferably, a pair of primer sequences involved in PCR amplification of the complex obtained in the last round of screening are shown in SEQ ID NO:23 and SEQ ID NO:24.

Further, a nucleic acid purification method comprises magnetic bead purification.

An aptamer of nattokinase, a nucleotide sequence of the aptamer is any one of SEQ ID NO: 1 to SEQ ID NO:17.

Further, the aptamer of nattokinase is obtained by any of the above screening methods.

A kit for molecular recognition of nattokinase protein, comprising the nattokinase nucleic acid aptamer of the above.

Compared with the prior art, the disclosure has the following advantages and beneficial effects.

Capillary electrophoresis technology is used to screen aptamers in the present disclosure. The screening efficiency has been significantly improved.

The avidity range of the seven aptamers is 8.7-87 nM, which has a strong affinity. The affinity value is calculated based on the dissociation constant and measured by the surface plasmon resonance technique. The nucleic acid aptamer provided by the present disclosure can be used as an effective molecular recognition tool for the highly sensitive analysis of proteins, because it has high specificity, high affinity, and convenient chemical modification. The recognition technology based on nucleic acid aptamers provides a basis for the development of NK determination and efficient separation and purification. Up to now, there is no related report of nattokinase aptamer.

The requirements of high accuracy, high sensitivity, and high specificity of NK analysis are met by using nattokinase aptamer to establish a concentration or activity determination method. Aptamers are used as molecular recognition tools to provide a key basis for the separation and purification of NK.

The interaction of candidate aptamer with target is explored through surface plasmon resonance technology. The dynamics and thermodynamics of molecular interactions are studied. These provide a key basis for the establishment of the aptamer evaluation system. The research in this application is helpful to develop the unique advantages of nucleic acid aptamers, and can promote the research progress in the fields of NK active sites, catalytic mechanism, separation and purification

DETAILED DESCRIPTION OF THE EMBODIMENTS

Figure 1:
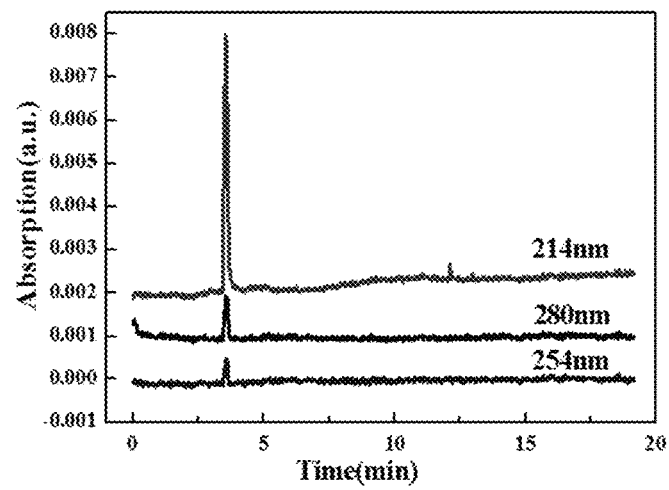
FIG. 1 shows a wavelength detection result of NK obtained in Example 1.

In order to make objects, technical solutions and advantages of the present disclosure clearer, the present disclosure is further described in detail with examples. The devices and reagents used in the examples are commercially available unless otherwise noted. The examples are only for explaining the present disclosure, not for limiting the present disclosure, since various modifications and substitutions can be made without departing from the present disclosure.

The genes, proteins or fragments thereof involved in the present disclosure may be natural purified products, or chemically synthesized products, or produced from prokaryotic or eukaryotic hosts (for example, bacteria, yeasts, plants) through recombinant technology.

The nucleic acid aptamer specifically binding to the nattokinase target screened in the present disclosure is a new aptamer. Capillary electrophoresis technology is used to screen aptamers in the present disclosure. The screening efficiency of aptamers has been significantly improved, and the problems of cumbersome, time-consuming, low-efficiency and poor repeatability of traditional screening methods have been solved. The interaction of candidate aptamer with target is explored through surface plasmon resonance technology and capillary electrophoresis technology. The dynamics and thermodynamics of molecular interactions are studied. These provide a key basis for the establishment of the aptamer evaluation system. The research in this application is helpful to develop the unique advantages of nucleic acid aptamers, and can promote the research progress in the fields of NK active sites, catalytic mechanism, separation and purification.

The aptamer of nattokinase and method for screening the aptamer are described in the following examples.

Example 1 Establishment of Experimental Conditions

Experimental conditions in the screening process were explored, such as the type of running buffer, the best detection wavelength, etc. Finally, 50 mmol/L boric acid-borax buffer (pH 7.8) was selected as the running buffer for capillary electrophoresis and the solvent for the nattokinase sample, and 280 nm was selected as the detection wavelength. The experimental process is as follows:

1. Establishment of Capillary Electrophoresis Analysis Method Suitable for Screening Nattokinase Aptamers Analysis conditions of capillary electrophoresis: Column temperature was 25° C., 0.5 psi, 20 s injection, separation under 25 kV voltage.

Activation of the capillary: before the capillary is first used, it is washed with methanol, 0.1 mol/L hydrochloric acid solution, regenerating solution (0.1 mol/L NaOH solution) and buffer in sequence. The washing conditions are: 20 psi, 3.5 min. When changing different solutions, ultrapure water is required. Flush for 2.0 min at 20 psi.

Cleaning of capillary: before each injection, the capillary is washed with ultrapure water and running buffer in sequence. Flushing conditions: 15 psi, 3.0 min. The capillary must be reactivated after being loaded several times. After ultrasonic treatment of the test reagent, it needs to be filtered with a 0.22 μm pore filter membrane before it can be used.

2. Confirmation Experiment of NK Wavelength

Detect and compare the response values of samples with a concentration of 1.00 mg/mL at three wavelengths of 214, 254 and 280 nm to obtain the best detection wavelength. 50 mmol/L boric acid-borax buffer (pH 7.8) was used as the running buffer.

FIG. 1 shows the experimental results. It can be seen from the figure that the sample response value at 214 nm is the strongest, followed by 280 nm, the weakest sample response at 254 nm. Because the interference at 214 nm is very serious, and the ultraviolet absorption wavelength of nucleic acid is at 254 nm, 280 nm is selected as the detection wavelength for capillary electrophoresis analysis.

3. Separation Experiment of NK, NK-ssDNA and ssDNA

Nattokinase and ssDNA (the 69 nt random sequence library below) were dissolved in 50 mmol/L boric acid-borax buffer (pH 7.8). The concentration of NK was 2.0 mg/mL and the concentration of ssDNA was 5 μmol/L. Capillary electrophoresis analysis was performed under the same conditions. The analysis conditions were the aforementioned optimized conditions.

Figure 2:
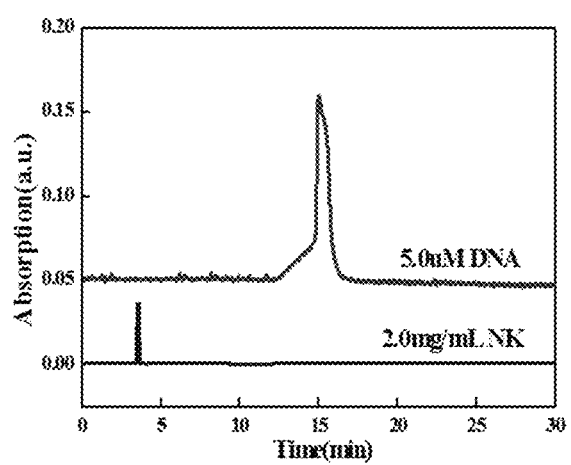
FIG. 2 shows a capillary electrophoresis separation diagram of NK and ssDNA obtained in Example 1.

FIG. 2 shows the experimental results. It can be seen from the figure that nattokinase peaks at 3.40 min to 3.67 min, while the peak time for ssDNA is 12.5 min to 16.5 min. Long peak interval indicates a good separation effect.

Figure 3:
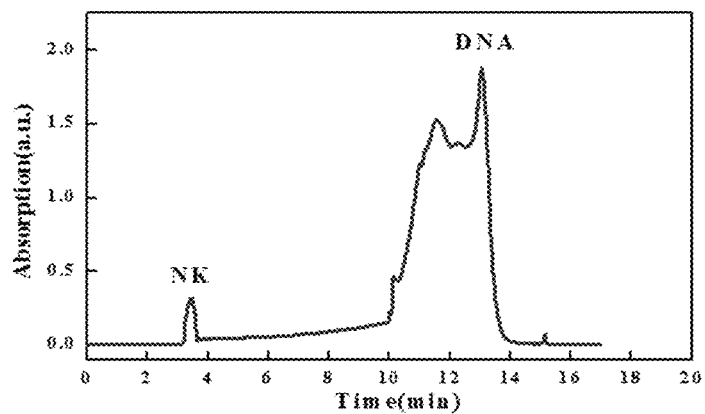
FIG. 3 shows a capillary electrophoresis separation diagram of mixture of NK and ssDNA obtained in Example 1.

A mixed solution of 0.005 mg/mL NK and 100 μmol/L ssDNA was prepared for capillary electrophoresis analysis, and the experiment was performed three times. FIG. 3 shows the experimental results. It can be seen from the figure that NK and ssDNA can be completely separated in the mixed solution.

4. Optimization of PCR Conditions

Figure 4:
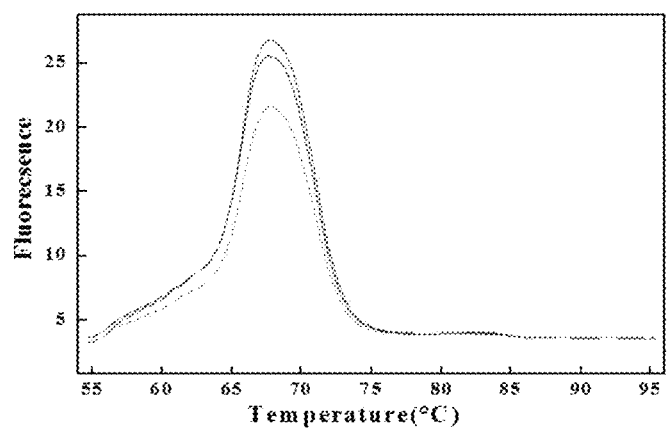
FIG. 4 shows an experimental result of the optimal annealing temperature in the PCR process in Example 1.
Figure 5:
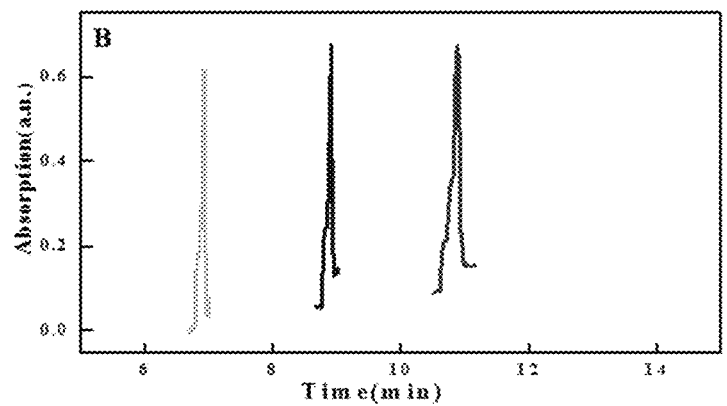
FIG. 5 shows a CE electropherogram of the PCR in Example 1.

Experiments under optimal amplification conditions: 55° C., 57° C., 59° C., 61° C., 63° C., 65° C. were used as annealing temperature, random sequence was used as template for PCR. After the range of 61-63° C. was selected as the optimal annealing temperature, 61° C., 62° C., and 63° C. were used as the annealing temperature for experiments. When the annealing temperature was 61° C., the dissolution curve had a peak at 62° C. and a peak at 82° C., but the peak was very small (FIG. 4). There is no impurity peak in CE electrophoresis (FIG. 5), which indicates that the specificity of the reaction is good at 61° C.

5. Optimization of Conditions for Preparing Secondary Libraries by Asymmetric PCR Under the best PCR conditions, the primer concentration and the ratio of the two primers are constantly changing (primer sequence is shown in Table 1). The experimental results show that the concentration of primer P2 is 0.5 μmol/L, and the primer ratio is 30:1. There are many asymmetric PCR products under this experimental condition. Although there were non-specific amplification products under this condition, specific amplification products can be well separated from non-specific products in gel electrophoresis, and can be used for gel recovery to prepare single-stranded secondary libraries.

Figure 6:
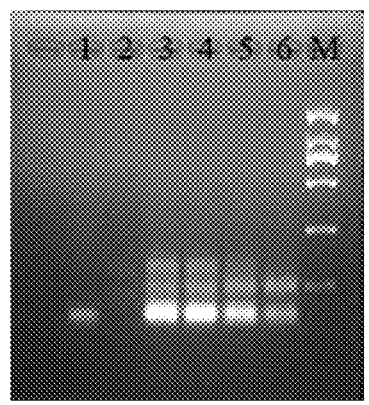
FIG. 6 shows an electropherogram of primer concentration ratio optimization in asymmetric PCR.

FIG. 6 shows the experimental results. Among them, the band: M. DL2000 DNA Marker; 1. ssDNA; 2. Blank control; 3-6 is the PCR product under the primer ratio: 3. 40:1, 4. 30:1, 5. 20:1, 6. 10:1.

6. Screening of NK Aptamers

The first round of screening is described as follows.

Before screening, the easily soluble random oligonucleotide library was denatured at 95° C. for no less than 10 minutes, and then slowly cooled to room temperature. After the random oligonucleotide library solution was cooled to room temperature, it was mixed with nattokinase. The concentration of nattokinase in the solution was about 0.0025 mg/ml (1.0 μmol/L). The mixture was incubated at 30° C. for no less than 30 minutes, and slowly mixed up and down every 20 minutes. The amount of nattokinase was sufficient to fully bind to the oligonucleotide chain that can bind to nattokinase in the random oligonucleotide library. After being placed at room temperature for 10 minutes, the sample was separated.

Figure 7:
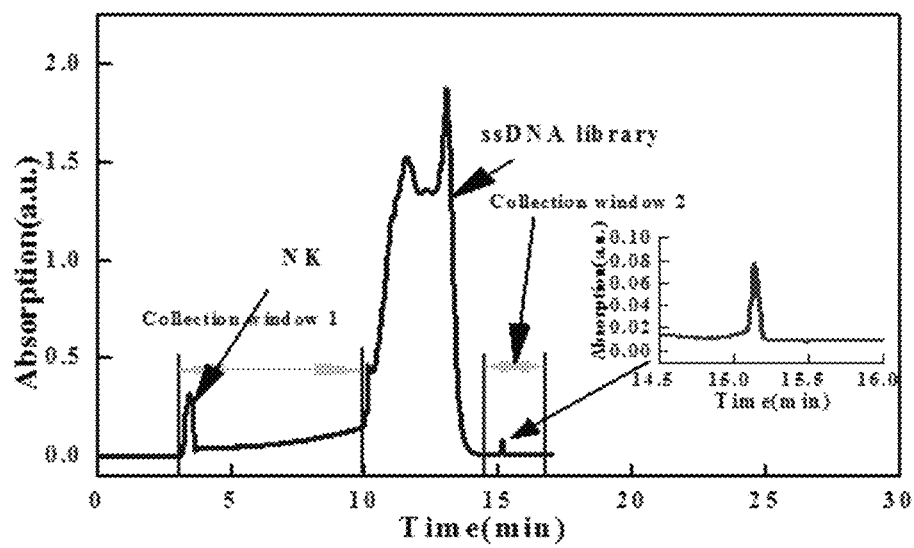
FIG. 7 shows a CE electropherogram of the first round of screening of NK nucleic acid aptamer screening experiment in Example 1.

The materials in collection window 1 and collection window 2 in FIG. 7 were collected and stored in a sample bottle containing 10 μL of running buffer. In order to make the concentration of nucleic acid in the product high enough, collect 10 times continuously.

It can be seen from the figure that as the concentration of the random oligo ssDNA library increases, the baseline between the target nattokinase and the free nucleic acid library peaks tends to drift upward. This may be caused by the continuous dissociation of the ssDNA-NK complex during the electrophoresis process to produce a "capillary coating". In the experiment, the "baseline drift" part and the peak position of the NK-ssDNA complex were collected at the same time.

The second round of screening are described as follows.

The NK-ssDNA complex collected in the first round of screening was used to replace the random nucleic acid library for the second round of nattokinase aptamer screening. The experimental conditions were consistent with the first round of screening. In the subsequent rounds of screening, the NK-ssDNA complexes collected in the previous round of screening were used to replace the random library. Aptamers with sufficient affinity for nattokinase were obtained through repeated screening.

Figure 8:
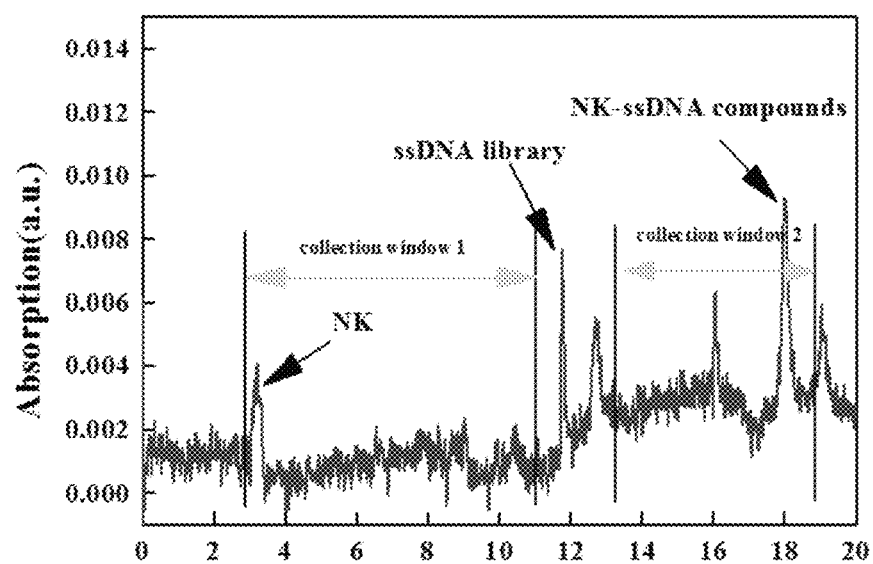
FIG. 8 shows a CE electropherogram of the second round of screening of NK nucleic acid aptamer screening experiment in Example 1.

In the second round of aptamer screening test, the collection of the first round was incubated with nattokinase. The solution was collected in sections after injection and analysis. The electrophoresis pattern collected by the aptamer was shown in FIG. 8.

The third round of screening are described as follows.

Figure 9:
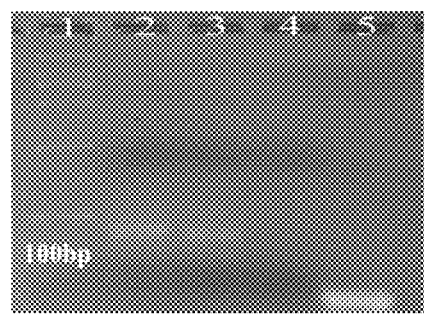
FIG. 9 shows a Gel electrophoresis image of the third round of screening of NK nucleic acid aptamer screening experiment in Example 1.
Figure 10A:
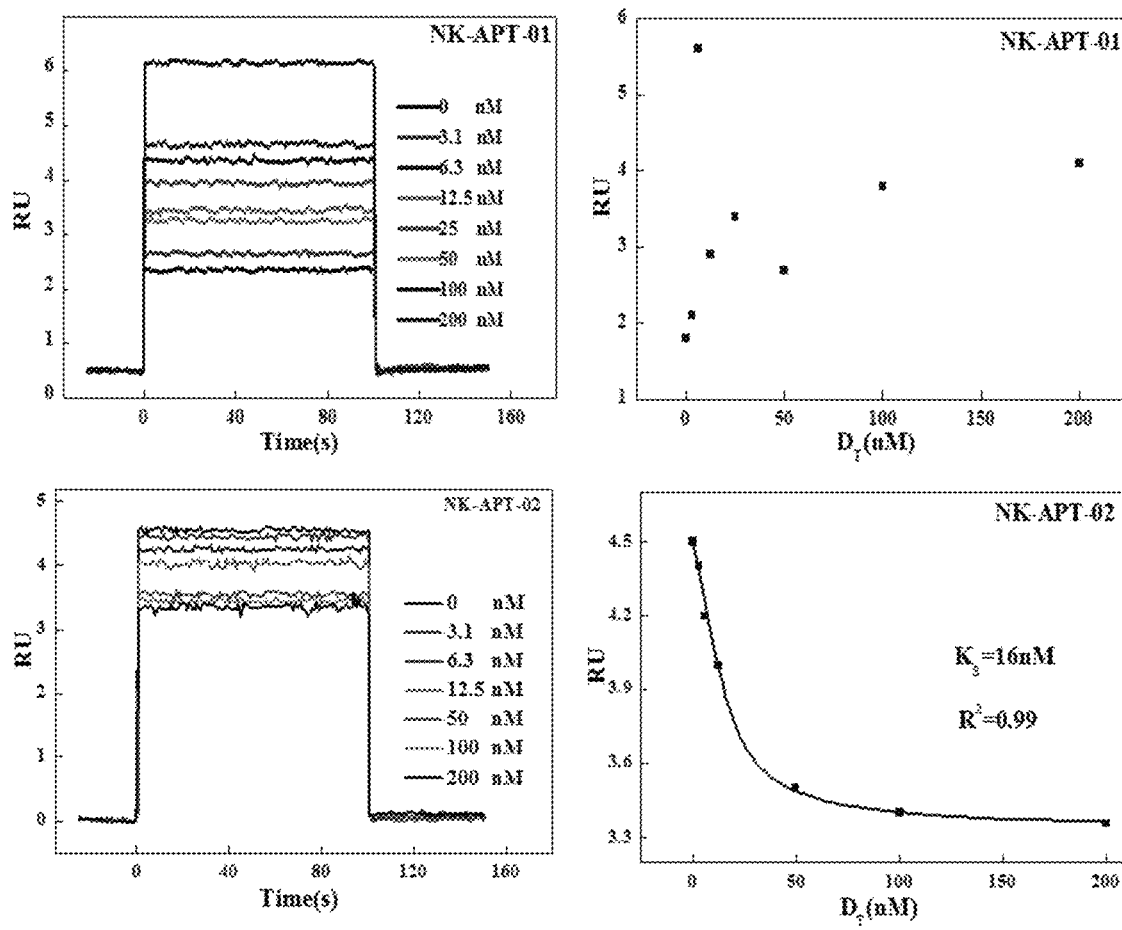
FIG. 10 including FIG. 10(*a*), FIG. 10(*b*), FIG. 10(*c*), FIG. 10(*d*), FIG. 10(*e*), FIG. 10(*f*), FIG. 10(*g*), shows affinity test result of NK nucleic acid aptamer in Example 2.
Figure 10B:
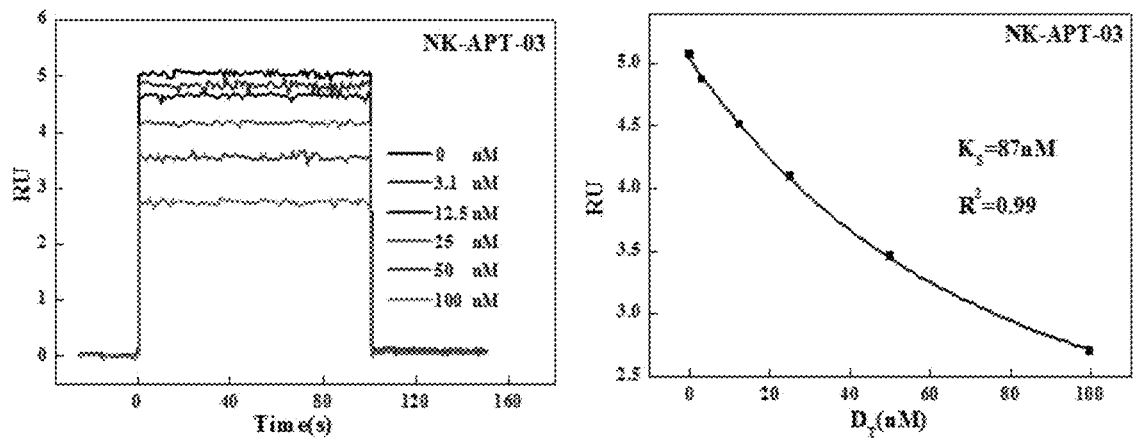
Figure 10C:
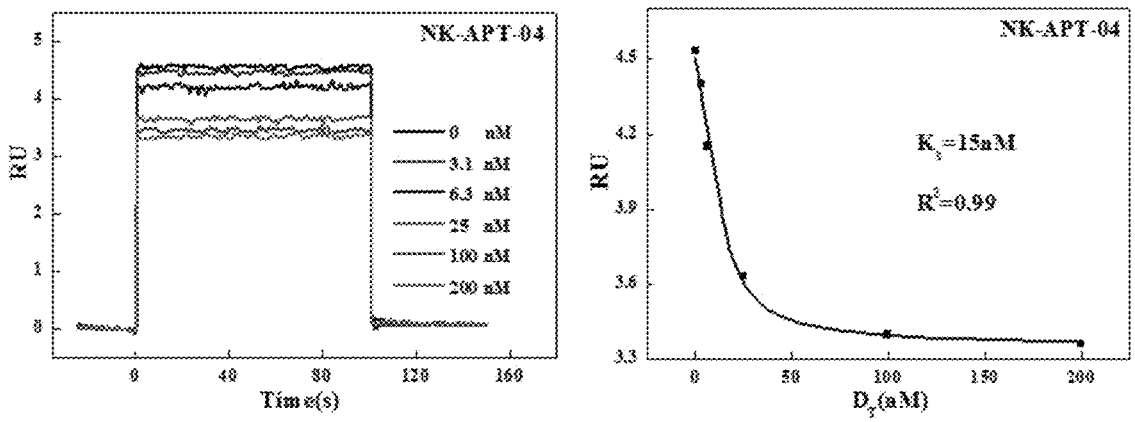
Figure 10D:
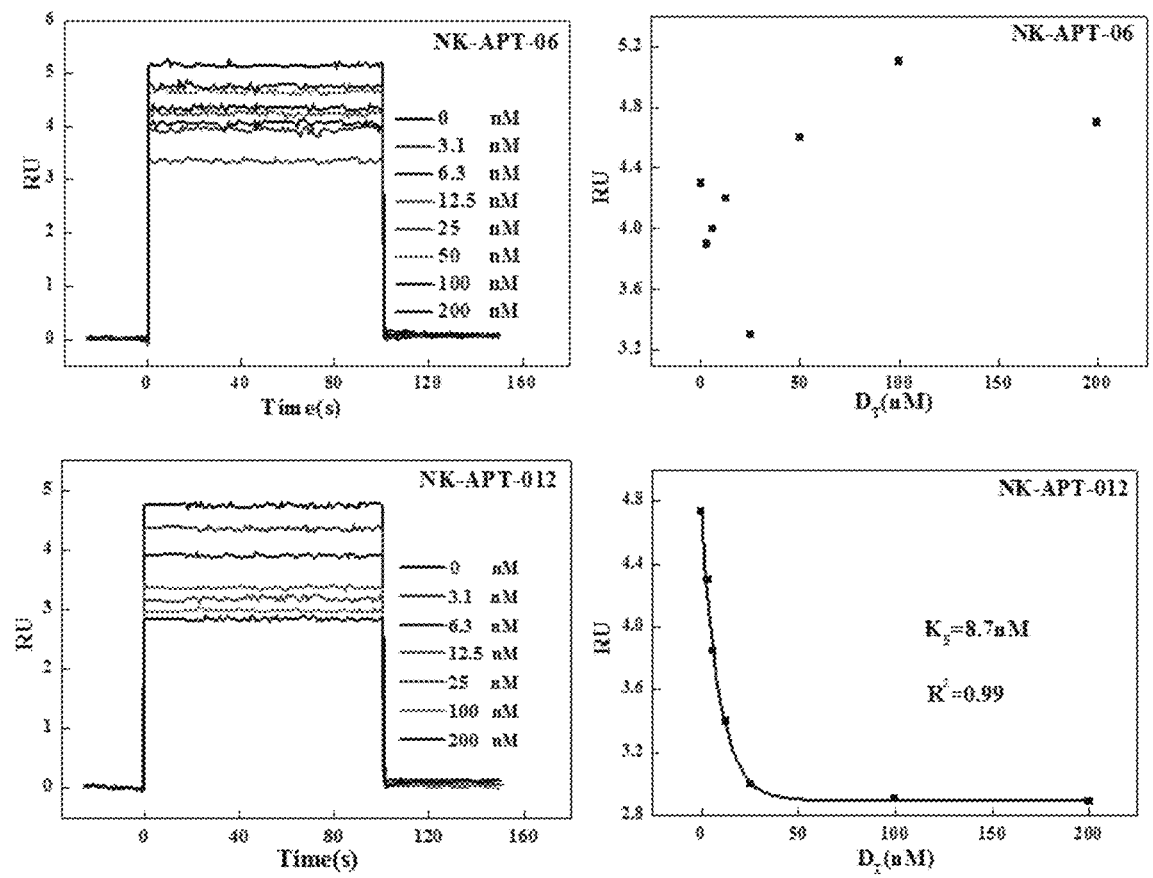
Figure 10E:
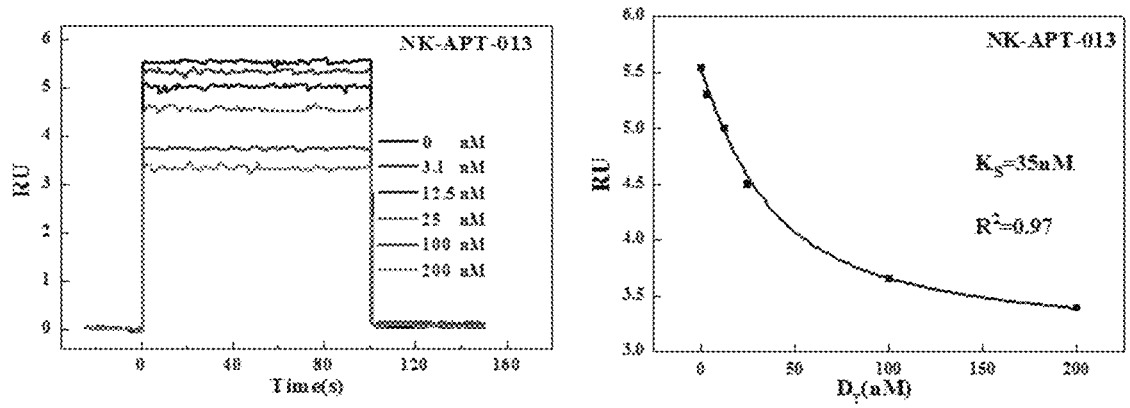
Figure 10F:
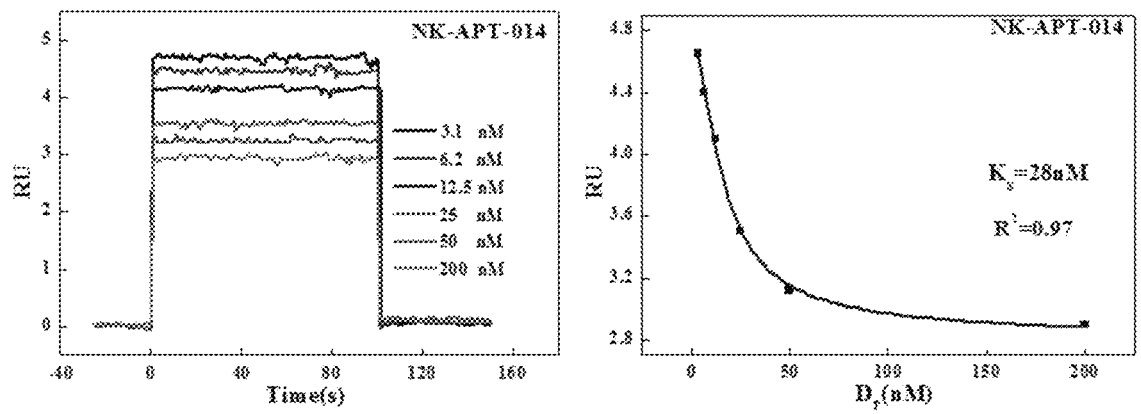
Figure 10G:
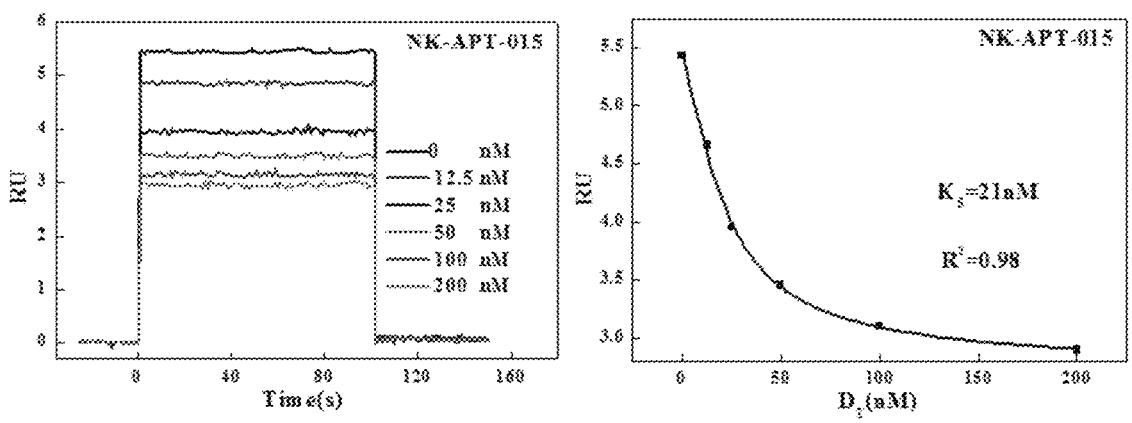
Figure 10G:
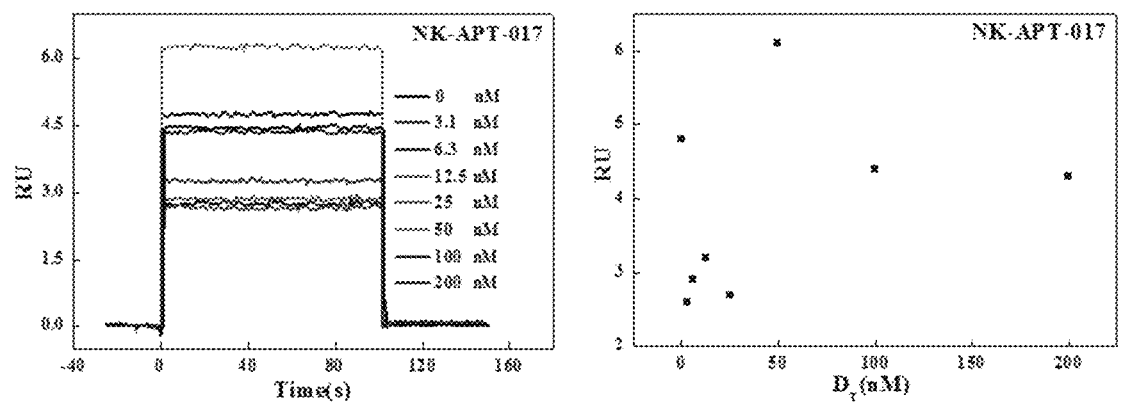

The NK-ssDNA complex collected in the second round of screening was used as a template for PCR amplification. The PCR system and procedures were shown in Table 2 and Table 3. 69 nt-ssDNA (sequence shown in Table 1) and ultrapure water were used as templates for control experiments. The results of PCR gel electrophoresis were shown in FIG. 9, where 1: identifying nucleic acid; 2:69 nt-ssDNA as template PCR product; 3: NK-ssDNA as template PCR product; 4: blank control; 5:69 nt-ssDNA.

It can be seen from the figure that the bands of the products amplified with 69nt-ssDNA library as template are basically the same as the bands of the collected NK-ssDNA complex samples. No scattering bands are produced, and these bands are located near the 100 bp mark. No product was formed in the blank control with ultrapure water as the template. This shows that the PCR amplification is successful, the collection contains NK-ssDNA complex, and the concentration is not higher than 1.0 nmol/Lol/mL. The ssDNA in the collected NK-ssDNA complex was successfully amplified. The third round of NK-ssDNA collection experiment was effective.

Example 2 Screening of Nattokinase Nucleic Acid Aptamer

The purchased nattokinase was purified by chromatography and identified. Aptamers were screened by using purified protein and experimental conditions determined in Example 1. The screening method is as follows.

1. Design of Nucleic Acid Library and Primers

The sequence required for the experiment was designed by the nucleic acid primer design software Primer, and the secondary structure of the designed nucleic acid strand was evaluated by the NUPACK software and The Mfold Web Server.

2. Nattokinase, Nucleic Acid and Complex Were Separated by Capillary Electrophoresis The concentration of the immobilized fluorescently labeled oligonucleotide library was 0.5 μmol/L, and the concentration of nattokinase was 0.125 μmol/L. After these two solutions were mixed, they were incubated at 30° C. under dark conditions. It was taken out every 10 minutes and shaken gently, and the sample was separated after 30 minutes. Separation conditions: capillary temperature was 25° C., 0.5 psi, 20 s injection, separation voltage 25 kV; before each injection, methanol, ultrapure water, 0.1 mol/L hydrochloric acid solution, ultrapure water, regenerant A (0.1 mol/L NaOH solution), ultrapure water, and running buffer were sequentially used for washing. Flushing conditions: 20 psi, 5.0 min; ultrapure water and running buffer were used for flushing between two injections. Flushing conditions: 15 psi, 3.0 min.

Nattokinase peaked at 3.3 min, and 69nt-ssDNA peaked at 9.9 min. The "baseline drift" part was collected in the time range of 3.96 min to 11.88 min. The peak of NK-ssDNA complex appeared at 15.2 min. The complex was collected in the time range of 18.76 min to 24.56 min.

3. After the Random Library was Combined with NK, the Secondary Library was Prepared by Asymmetric PCR.

The nucleic acid sequences of the primers and templates used in the PCR system were shown in Table 1.

TABLE 1

Sequence and length used in PCR system

| name | Sequence (5'-3') | Length (nt) |
|---|---|---|
| Upstream primer ($P_1$) | 5'-ACGACGAGACACCTGACATC-3' SEQ ID NO: 18 | 20 |
| downstream primer ($P_2$) | 5'-TTGAGCCTACGAGCGATACC-3' SEQ ID NO: 19 | 20 |
| Fixed sequence (gdDNA) | 5'-TTGAGCCTACGAGCGATACCGAGTGACAATCGACACATATTAGTATCTTC AACCCGTAGATGTCAGGTGTCTCGTCGT-3' SEQ ID NO: 20 | 78 |
| 80nt Random sequence (80nt-ssDNA) | 5'-TTGAGCCTACGAGCGATACC-40N-GATGTCAGGTGTCTCGTCGT-3' SEQ ID NO: 21, 40N is a random sequence of 40 T, G, A, C. | 80 |
| 69nt Random sequence (69nt-ssDNA) | 5'-TTGAGCCTACGAGCGATACC-29N-GATGTCAGGTGTCTCGTCGT-3' SEQ ID NO: 22, 29N is a random sequence of 29 T, G, A, C | 69 |

The various substances used in the PCR system and their concentrations were shown in Table 2.

TABLE 2

PCR reaction system

| Reagent | The initial concentration | volume (μL) |
|---|---|---|
| ddH$_2$O | Pure water | 4.5 |
| $P_1$ | 2.0 μmol/L | 7.5 |
| $P_2$ | 2.0 μmol/L | 7.5 |
| Target | 1.0 nmol/Lol/L | 3.0 |
| PCR Master Mix |  | 25 |
| Eva Green |  | 2.5 |
| Total volume |  | 50 μL |

The basic reaction procedures of the PCR system were shown in Table 3.

TABLE 3

Basic PCR reaction procedures

| Number of cycles | transsexual | annealing | extend |
|---|---|---|---|
| 1 | 94° C., 1 min | | |
| 2-30 | 94° C., 30 s | 61° C., 20 s | 72° C., 10 s |
| 31 | | | 72° C., 5 min |

Asymmetric PCR system and procedures were shown in Table 4 and Table 5.

TABLE 4

Asymmetric PCR reaction system

| Reagent | The initial concentration | volume (μL) |
|---|---|---|
| ddH$_2$O | | 12.25 |
| $P_1$ | 5 μmol/L | 7.5 |
| $P_2$ | 0.5 μmol/L | 2.25 |
| Target | 1.0 nmol/L | 3.0 |
| PCR Master Mix | | 25 |
| Total volume | | 50 μL |

TABLE 5

| | Asymmetric PCR program | | |
|---|---|---|---|
| Number of cycles | transsexual | annealing | extend |
| 1 | 94° C., 1 min | | |
| 2-25 | 94° C., 30 s | 61° C., 20 s | 72° C., 10 s |
| 26 | | | 72° C., 5 min |

4. The complex or secondary library (the secondary library can also be screened for multiple rounds according to the optimized conditions) obtained in the previous screening was used for PCR amplification, so that the pure nucleic acid combined with nattokinase was obtained. In this embodiment, the secondary library obtained by asymmetric PCR was used as a template for amplification. Specific operations: Genomic DNA was accurately quantified using Qubit 2.0 DNA detection kit, and the amount of DNA that should be added to the PCR reaction was determined. Illumina bridge PCR compatible primers were introduced into the primers used in PCR.

190294-F: AGCAGCACAGAGGTCAGATG, SEQ ID NO: 23.
190294-R: TTCACGGTAGCACGCATAGG, SEQ ID NO: 24.

PCR system was as follows.

| Reagent | volume |
|---|---|
| 2 × Taq master Mix | 15 μL |
| Bar-PCR primer F(10 uM) | 1 μL |
| Primer R (10 uM) | 1 μL |
| PCR products (Last round) | 10-20 ng |
| H₂O | add to 30 μL |

PCR program was as follows.

| | Asymmetric PCR program | | |
|---|---|---|---|
| Number of cycles | transsexual | annealing | extend |
| 1 | 94° C., 1 min | | |
| 2-25 | 94° C., 30 s | 61° C., 20 s | 72° C., 10 s |
| 26 | | | 72° C., 5 min |

Table 1. Sequence and length used in PCR system

5. Purify the Amplified Nucleic Acid

The specific operation was as follows.

1) Magnetic beads were added to 40 μL PCR product at a dose of 0.6-0.8 times (refer to Bioengineering Magnetic Bead Method Sequencing Product Purification Kit). The magnetic beads were adsorbed on the magnetic stand for 5 minutes after shaking and fully suspended, the supernatant was sucked out with a pipette.
2) Magnetic beads were added to the remaining solution at a dose of 0.6-0.8 times. The magnetic beads were adsorbed on the magnetic stand for 5 minutes after shaking and fully suspended, the supernatant was sucked out with a pipette.
3) 90 μL WashBuffer (or 70% ethanol) was added to the remaining solution, the PCR tube was placed on the magnetic stand in the reverse direction, the magnetic beads were adsorbed to the other side of the PCR tube, and the supernatant was sucked out after sufficient adsorption.
4) The PCR tube or 8-strip tube was placed in a 55° C. oven for 5 minutes to completely volatilize the alcohol inside.
5) 30 μL Elution Buffer was added for elution.
6) The PCR tube was placed on the adsorption rack for 5 minutes. After fully adsorption, the supernatant was transferred to a clean 1.5 mL centrifuge tube for quantitative use.
7) The purified nucleic acid was accurately quantified using Qubit2.0 DNA detection kit to facilitate sequencing after mixing in an equal amount of 1:1. The amount of DNA of each sample was 10 ng and the same amount is mixed, and the final sequencing concentration on the computer was 20 pmol.
8) Finally, 17 candidate nucleic acid aptamers were obtained, the sequence was as follows.

NK-APT-01 CGCCTGAGGGATGACCTGTTCATGTAGGG SEQ ID NO: 1.
NK-APT-02 GACTACCGCGGAGATCTCCAATCGGGATG SEQ ID NO: 2.
NK-APT-03 AAATGAGGACCTCATTATCTTAGGAAGGT SEQ ID NO: 3.
NK-APT-04 GCCTTAAAAACGTCCTTAGTGACGTTTAC SEQ ID NO: 4.
NK-APT-05 GCTCACGTAGATTAAACTATGCTAAGAGC SEQ ID NO: 5.
NK-APT-06 CATTGCAATGTAACTGTCTAGCTTGACTG SEQ ID NO: 6.
NK-APT-07 CCGGTCGCCATGGGGGAGCTGCGTACCGC SEQ ID NO: 7.
NK-APT-08 CCATTCCAACTCGCTTTAAACATAAATCG SEQ ID NO: 8.
NK-APT-09 CTGTGAACCAAGGATTCATGCCGGTAAAC SEQ ID NO: 9.
NK-APT-10 GGGTTACGATCAGTCTCATGGAAACGACC SEQ ID NO: 10.
NK-APT-11 GTTGCAAGGAAAGCTATGCCTATGCCCCA SEQ ID NO: 11.
NK-APT-12 CTCGTGTAAAACGATGGTAGCTGTACTTG SEQ ID NO: 12.
NK-APT-13 AAAGGCGCTGTGCACAGTGTCCCCGCGGG SEQ ID NO: 13.
NK-APT-14 CCGAGGGGAATTCACCACGAATCGCCTCT SEQ ID NO: 14.
NK-APT-15 TCGATAGTTGTACTGGAGTGAATCACTGA SEQ ID NO: 15.
NK-APT-16 AAGACTCCAGTCGCGGCCTCTATCCGGGA SEQ ID NO: 16.
NK-APT-17 ACCCAAGTAGGCGAGTTCAGAACTGTGTG SEQ ID NO: 17.

6. The secondary structure of the obtained sequence was analyzed by Mfold software at 25° C. and Na⁺ of 50 mmol/L. The results showed that the obtained sequence generally had a neck loop structure. The affinity of the seven candidate aptamers with higher affinity was initially identified using CE-fluorescence detection technology.

First, the nucleic acid library without nattokinase was subjected to CE analysis. After adding nattokinase, perform CE electrophoresis analysis before and after incubation. The affinity was expressed by the percentage change in peak area $S=(A_0-A_1)/A_0$, where $A_0$ was the peak area of the nucleic acid library, and $A_1$ was the peak area of the nucleic acid library that was not bound to the target after incubation with the target nattokinase. The larger the ratio, the greater the affinity between nattokinase and the nucleic acid library.

The specific operation was as follows. Nucleic acid aptamers with representative secondary structures were synthesized by 5'6-FAM (FITC) fluorescent labeling. The aptamer was diluted to 0.5 μmol/L with 50 mmol/L pH7.8 boric acid buffer. The easily soluble random oligonucleotide library was denatured and placed at 95° C. for no less than 10 min, and then slowly cooled to room temperature. 50 μL of nucleic acid aptamer solution was added to 10 μL of nattokinase solution with a concentration of 0.05 mg/mL, and the solution was made up to 100 μL with 50 mM pH7.8 boric acid buffer to obtain an aptamer concentration of 0.25 μmol/L and NK concentration of 0.005 mg/mL mixture. Incubate the mixture at 30° C. for 30 min and load the sample for analysis.

Figure 12:
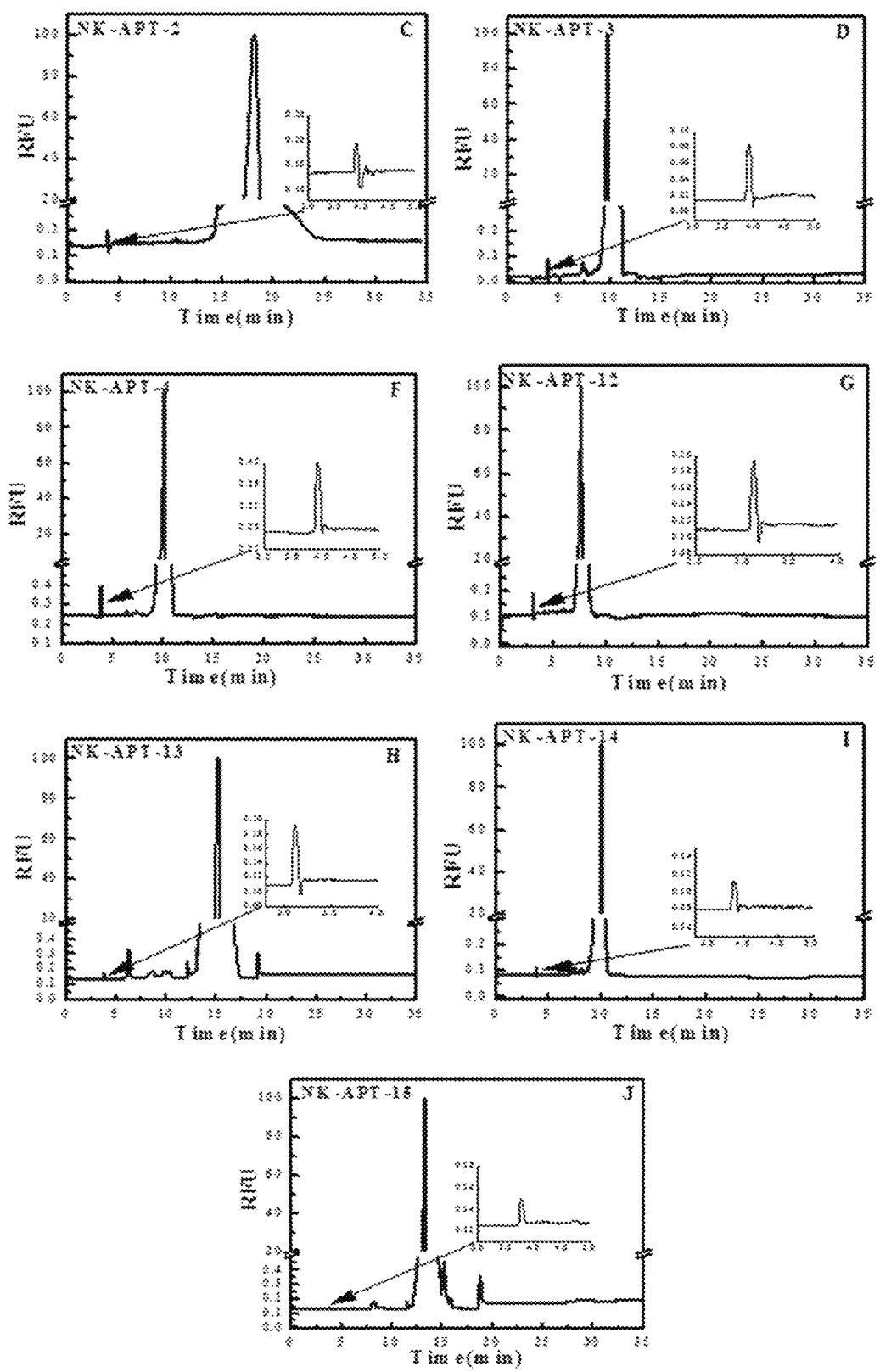
FIG. 12 shows CE electrophoresis analysis results of affinity in Example 2.

FIG. 12 was a capillary electrophoresis diagram of seven aptamers and complexes provided by an embodiment of the present disclosure. The surface binds to nattokinase with a strong affinity. In the figure: (a), SEQ ID NO: 2; (b), SEQ ID NO: 3; (c), SEQ ID NO: 4; (d), SEQ ID NO: 12 (e), SEQ ID NO: 13; (f), SEQ ID NO: 14; (g), SEQ ID NO: 15.

7. The Identification of the Affinity of the Candidate Aptamer and Nattokinase was as Follows.

Measurement conditions of steady-state affinity: Temperature: 4° C., flow rate: 30 μl/min, binding time: 100 s, dissociation time: 100 s. 0-220 nmol purified NK was flowed through the chip in sequence, and an obvious steady-state response graph of SPR was obtained. The response value obtained in the equilibrium state was used for nonlinear fitting of different protein concentrations. The affinity KC of the protein-aptamer on the chip was 5.4 nmol/Lol/L.

NK with a concentration of 2KC was prepared and mixed with ten competing aptamers of different concentrations. Different SPR response values were obtained on the same chip, and nonlinear fitting was performed to obtain the KS of the other nine aptamers in solution. The concentration gradient of competing aptamers ranges from 0-200 nmol/L. FIG. 10 shows the results of nonlinear fitting. The experimental data were shown in Table 6.

TABLE 6

The affinity constant KS of the ten aptamers screened

| name | $K_S$ (nmol/L) | $R^2$ |
| --- | --- | --- |
| NK-APT-01 | — | — |
| NK-APT-02 | 16 | 0.99 |
| NK-APT-03 | 87 | 0.99 |
| NK-APT-04 | 15 | 0.99 |
| NK-APT-06 | — | — |
| NK-APT-12 | 8.7 | 0.99 |
| NK-APT-13 | 35 | 0.97 |
| NK-APT-14 | 28 | 0.97 |
| NK-APT-15 | 21 | 0.98 |
| NK-APT-17 | — | — |

7. Specific Determination of NK Nucleic Acid Aptamer

Figure 11:
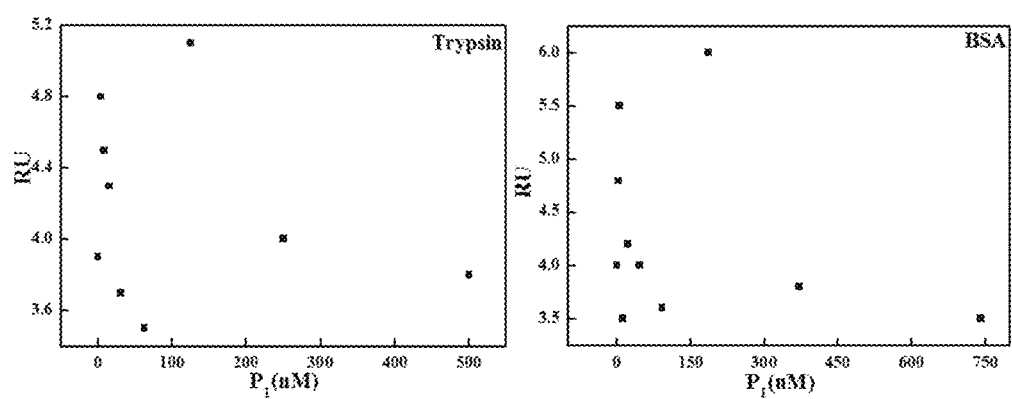
FIG. 11 shows specificity determination result of NK nucleic acid aptamer in Example 2.

Different concentrations of bovine serum protein and trypsin were passed through the chip, and the response values obtained under the same conditions are shown in FIG. 11.

The results showed that as the protein concentration increased, the SPR response value did not increase accordingly. It can be inferred that this aptamer did not bind to bovine serum protein and trypsin or had a weak binding force.

It is understood that the examples described herein are for illustrative purposes only, not for limiting the present disclosure. The various modifications, equivalent replacements and improvements made without departing the spirit and principle of the present disclosure should be all encompassed in the protection scope of the present disclosure. All publications, patents, and patent applications cited herein are hereby incorporated by reference in their entirety for all purposes.

What is claimed is:

1. An aptamer of nattokinase, wherein the aptamer consists of a nucleotide sequence represented by any one of SEQ ID NO: 1 to SEQ ID NO:17.

2. A kit for molecular recognition of nattokinase protein, comprising the aptamer of nattokinase of claim 1.

* * * * *